United States Patent [19]

Tuinstra et al.

[11] Patent Number: 4,973,728

[45] Date of Patent: Nov. 27, 1990

[54] PREPARATION OF AROMATIC CARBONATES

[75] Inventors: Hendrik E. Tuinstra, Midland; Cynthia L. Rand, Sanford; Edmund P. Woo, Midland, all of Mich.

[73] Assignee: The Dow Chemical Company, Midland, Mich.

[21] Appl. No.: 84,358

[22] Filed: Aug. 12, 1987

[51] Int. Cl.$^5$ .................... C07C 68/06; C07C 69/96
[52] U.S. Cl. ................... 558/268; 528/370; 558/270; 558/277
[58] Field of Search ............ 558/268, 270, 277

[56] References Cited

U.S. PATENT DOCUMENTS

| | | | |
|---|---|---|---|
| 4,182,726 | 1/1980 | Illuminate et al. | 558/270 |
| 4,349,486 | 9/1982 | Brunelle et al. | 558/270 |
| 4,609,501 | 9/1986 | Mark | 558/270 |

*Primary Examiner*—Vivian Garner

[57] ABSTRACT

Aromatic carbonates useful for the preparation of high molecular weight polycarbonate resins are prepared by reacting methanol, carbon monoxide and oxygen to prepare dimethyl carbonate; reacting a methyl silyl ether with a phenol or bisphenol to prepare an aryl silyl ether, and reacting the dimethyl carbonate and aryl silyl ether to prepare an aromatic carbonate.

10 Claims, No Drawings

PREPARATION OF AROMATIC CARBONATES

BACKGROUND OF THE INVENTION

The reaction of phenol or bisphenols with dialkyl carbonates is slow leading to long reaction times even when catalyzed by various Lewis acids. Many catalysts including various titanates and stannates have been described for use in the above mentioned reaction. Examples may be found in U.S. Pat. Nos. 4,252,737; 4,182,726; 4,552,704; as well as German laid open applications DE Nos. 2,736,063 and 2,736,062.

Somewhat faster transesterification reaction rates are obtained by the utilization of phenyl acyl esters or bisphenyl acyl diesters. Examples of the foregoing may be found in U.S. Pat. Nos. 4,182,726 and 4,452,968. The teachings of all of the foregoing United States Patents are incorporated herein by reference thereto.

In U.S. Pat. No. 4,452,968 an integrated process for the preparation of aromatic polycarbonates was disclosed wherein the methyl acetate by-product formed in the transesterification of a bisphenol diacetate with a dialkyl carbonate was recycled by heating the alkyl ester to form a ketene and subsequently such ketene was reconverted by reaction with a bisphenol to form additional quantities of the bisphenol diacetate. For the teachings contained therein the above identified patent is incorporated herein by reference thereto.

However the preparation of a ketene intermediate involves high temperatures, and does not attain efficiencies of operation sufficient to permit successful commercialization of such an integrated process as is disclosed in U.S. Pat. No. 4,452,968.

It would be desirable if there were provided a process for preparation of aromatic carbonates, including methyl aryl carbonates, arylene bis (methyl carbonates and aromatic polycarbonates that allows for ease of conversion of phenol and bisphenol reactants, and high efficiency in the regeneration of the derivatizing agent.

SUMMARY OF THE INVENTION

According to the present invention there is now provided an improved process for the preparation of aromatic carbonate products comprising the steps of:

A. reacting a silyl ether corresponding to the formula $(CH_3O)_mSiR_{4-m}$ or $R'_3SiOSiR'_3$ wherein R is hydrogen, $C_{1-6}$ alkyl or haloalkyl, R' is $C_{1-6}$ alkyl or haloalkyl and m is an integer from one to three with an aromatic hydroxyl containing compound of the formula $Ar(OH)_n$, wherein Ar is a $C_{6-20}$ aromatic or substituted aromatic radical, and n is one or two to prepare an aryl silyl ether or an arylene bis(silyl ether);

B. reacting dimethyl carbonate with at least a portion of the aryl silyl ether or arylene bis(silyl ether) of step A to prepare a methyl aryl carbonate or an arylene bis(methyl carbonate) and a methyl silyl ether; and C. recycling at least a portion of the methyl silyl ether produced in step B for use as the silyl ether reactant in step A.

The aromatic carbonate product of step B may be easily converted to the corresponding aromatic polycarbonate by well known techniques. Arylene bis(methyl carbonates) form aromatic polycarbonates merely upon heating. Methyl aryl carbonates may be converted to diaryl carbonates by heating and the diaryl carbonate may subsequently be reacted with a bisphenol to form the corresponding aromatic polycarbonates. Higher molecular weight polymers are produced by continued heating of the initially prepared oligomeric product.

DETAILED DESCRIPTION OF THE INVENTION

Suitable hydroxyaryl reactants for the present process include phenols and bisphenols previously known in the art for use in the preparation of aromatic carbonates. By the term bisphenol is also included inertly substituted bisphenols. A preferred monohydroxyaryl reactant is phenol. Examples of suitable bisphenol reactants include bisphenol-A, bisphenol-F, bisphenol-K, dihydroxy biphenyl, and halo, or $C_{1-6}$ alkyl substituted derivatives of the foregoing. A preferred dihydroxy aromatic reactant is bisphenol-A.

Silyl ethers for use according to the present invention preferably are methyl silyl ethers containing one or two methoxy groups, e.g. compositions corresponding to the formula $(CH_3O)_mSi(R)_{4-m}$ wherein m is one or two. A most preferred methyl silyl ether is methyl trimethylsilyl ether.

The reaction of a silyl ether with phenols or bisphenols according to step A of the aforementioned process is readily forced to completion by removal of volatile byproducts, suitably by the use of distillation. This step of the process may be illustrated for various silyl ether reactants by the following schematic diagram:

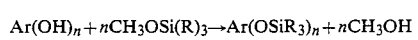

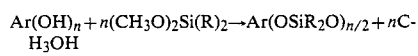

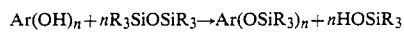

wherein Ar, R and n are as previously defined.

Preferred process conditions for the above ether exchange include the use of temperatures from about 20° C. to about 100° C., and a catalyst, particularly a protic acid such as p-toluenesulfonic acid or a macroporous ion exchange resin in the acid form.

Dimethyl carbonate for use in step B of the present invention may be prepared by the reaction between methanol, carbon monoxide and oxygen as taught for example in U.S. Pat. Nos. 3,846,468, 3,980,690, 4,452,968, 4,533,504, and 4,360,477, the teachings of which are incorporated herein by reference thereto. The reaction is generally expedited by the use of a catalyst, particularly a copper complex and the use of elevated temperatures and pressures.

The transesterification reaction between dimethyl carbonate and the aromatic silyl ether causes the formation of a methyl silyl ether coproduct. Removal of the methyl silyl ether coproduct drives the transesterification to completion and at the same time a suitable derivatizing agent is regenerated for reuse. This facile regeneration of derivatizing agent is in marked contrast with the cumbersome and ineffecient regeneration of a ketene intermediate required by prior art processes. The process operates at extremely high efficiencies and offers distinct advantages in product yields over alternative transesterification schemes for the preparation of aromatic carbonates and ultimately of polycarbonate resins.

In a highly desirable embodiment of the present invention, the reaction of the aryl silyl ether or arylene bis(silyl ether) with dimethyl carbonate is conducted in the presence of a catalyst, particularly a Lewis acid.

Preferred Lewis acids correspond to the formula $R''_pX(OR'')_{y-p}$, wherein $R''$ independently each occurrence is hydrocarbyl of from 1 to 10 carbons, X is a tin or titanium ion, p is a number from zero to y equal to the average number of $R''$ groups, and y is the valence of X. Preferrably amounts of such catalyst from about 0.01 to about 5.0 weight percent are employed.

It may be readily observed that the present process scheme allows for the overall conversion of a bisphenol to the corresponding polycarbonate utilizing dimethyl carbonate as the sole reactant consumed by the process. The recycle of methyl trimethylsilyl ether intermediate allows for great economy and simplicity in the resulting process compared to the generation of a ketene intermediate. The present process utilizes much lower reaction temperatures and results in greatly improved efficiency of operation.

In a further embodiment of the invention the synthesis of dimethyl carbonate may be integrated as part of the total process. In this embodiment, the present invention allows for a simplified and highly efficient route to the preparation of polycarbonates from bisphenols, methanol, carbon monoxide and oxygen. This embodiment of the invention may be more particularly described by the following steps:

A1. reacting methanol with carbon monoxide and oxygen to produce dimethyl carbonate and water;

A2. reacting a silyl ether corresponding to the formula $(CH_3O)_mSiR_{4-m}$ or $R'_3SiOSiR'_3$ wherein R is hydrogen, $C_{1-6}$ alkyl or haloalkyl, $R'$ is $C_{1-6}$ alkyl or haloalkyl and m is an integer from one to three with an aromatic hydroxyl containing compound of the formula $Ar(OH)_n$, wherein Ar is a $C_{6-20}$ aromatic or substituted aromatic radical, and n is one or two to prepare an aryl silyl ether or an arylene bis(silyl ether);

B. reacting at least a portion of the dimethyl carbonate of step A1 and at least a portion of the aryl silyl ether or arylene bis(silyl ether) of step A2 to prepare a methyl aryl carbonate or an arylene (bis methyl carbonate) and methyl silyl ether; and C. recycling at least a portion of the methyl silyl ether produced in step B for use as the silyl ether reactant in step A2.

Dimethyl carbonate may be recovered from the process upon conversion of the carbonate products of step B into polycarbonates. Such dimethyl carbonate by-products may be recycled and employed in step B.

Having described the invention, the following examples are provided as further illustrative and are not to be construed as limiting.

Bisphenol-A Trimethylsilyl Ether Preparation

The bisphenol-A trimethylsilyl ethers utilized in the following examples were prepared by either of the following two methods:

A. Bisphenol-A (22.8 g), hexamethyldisiloxane (250 mL) and p-toluene sulfonic acid were refluxed under nitrogen in a 500 mL round bottom flask equipped with a Soxhlet TM extractor containing activated 4 angstrom molecular sieves. To continuously remove water by-product, the sieves were exchanged at 12 hour intervals. To compensate for the volume of hexamethyldisiloxane trapped in the used sieves, 10 mL of hexamethyldisiloxane was also added at each exchange. Complete conversion of phenolic groups was achieved after 120 hours. The reaction mixture was cooled to room temperature and 20 g of dried $K_2CO_3$ was added. Following filtration through sintered glass, the reaction mixture was concentrated to a clear light yellow liquid which was distilled at 120° C. (0.15 mmHg) to give 35.24 g of 99% (1-methylethylidene)bis(4,1-phenyleneoxy)bistrimethylsilane.

B. A 50 mL round bottomed flask equipped with Dean Stark trap was charged with bisphenol-A (1.14 g), methoxytrimethylsilane (5 mL), and p-toluenesulfonic acid (0.10 g). The reaction mixture was heated to reflux and as material collected in the Dean Stark trap an equal volume of methoxytrimethylsilane was added. Complete conversion to the bis-silyl ether was obtained after the addition of 7 mL of methoxytrimethylsilane. The product was isolated in high yields by the above described procedure.

EXAMPLE 1

In an argon dry box a Fisher-Porter bottle (70 ml) equipped with a stir bar and pressure head is charged with (1-methylethylidene)bis(4,1-phenyleneoxy)bis-trimethylsilane (5.54 g; 15 mmol), dimethyl carbonate (40 ml; 0.454 mol), tetraphenyl titanate (0.063 g; 0.15 mmol; 1 mol percent), and triphenylmethane (1.7012 g; gc internal standard). The reactor is sealed and removed from the dry box. At time $t_0$, the reactor is immersed in an oil bath at 190° C. and at reflux a pressure of 60 psi is generated. During the course of the reaction 50 μl samples were withdrawn via air tight syringe. These aliquots were diluted with dimethyl carbonate and analyzed by gas/liquid chromatography (GLC). The results are given below in weight percent composition and as weight percent conversion of $ArOSiMe_3$ to $ArOCO_2Me$.

TABLE I

| Time | COMPONENT (%) | | | | | | % $ArOSiMe_3$ |
|---|---|---|---|---|---|---|---|
| (hrs) | 1 | 2 | 3 | 4 | 5 | 6 | conversion |
| .25 | .3 | 3.0 | 94 | 3 | 0.0 | 0.0 | 1.4 |
| .50 | .3 | 3.5 | 88 | 9 | 0.2 | 0.1 | 5 |
| 1 | .3 | 3.2 | 80 | 16 | 0.8 | 0.2 | 9 |
| 2 | .2 | 1.4 | 70 | 24 | 2 | 0.4 | 14 |
| 3 | .2 | 2.7 | 64 | 29 | 4 | 0.5 | 19 |
| 6 | .2 | 3.0 | 57 | 34 | 5 | 0.6 | 22 |

TABLE I-continued

| Time | COMPONENT (%) | | | | | | % ArOSiMe₃ |
|---|---|---|---|---|---|---|---|
| (hrs) | 1 | 2 | 3 | 4 | 5 | 6 | conversion |
| 14 | .2 | 3.0 | 51 | 38 | 7 | 0.8 | 26 |

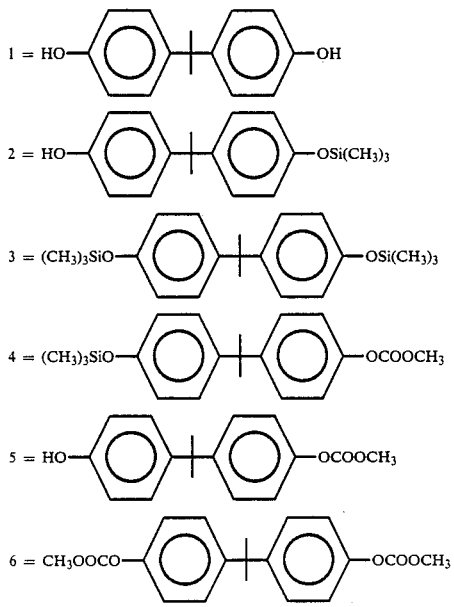

EXAMPLE 2

In a dry box the same reagents as described in Example 1 were charged into the Fischer-Porter bottle, the apparatus was flushed with nitrogen and the back pressure regulator was set to 80 psi with nitrogen to remove methanol-dimethyl carbonate azeotrope. The reactor was immersed in a 220° C. oil bath and dimethyl carbonate (dried over calcium hydride) was added at a rate sufficient to maintain constant volume in the reactor. The data obtained over a 7 hour period is shown in Table II. The components are identical to those of Example 1. After an extended period of reaction (18 hours) 77 percent conversion was obtained.

TABLE II

| Time | COMPONENTS (%) | | | | | | % |
|---|---|---|---|---|---|---|---|
| (Hrs) | 1 | 2 | 3 | 4 | 5 | 6 | Conversion |
| 1.00 | 0 | 10 | 68 | 0 | 20 | 0 | 10 |
| 1.75 | 0 | 12 | 65 | 0 | 23 | 0 | 12 |
| 2.50 | 0 | 13 | 57 | 2 | 26 | 3 | 17 |
| 4.00 | 0 | 11 | 47 | 3 | 30 | 6 | 23 |
| 5.00 | 0 | 13 | 38 | 5 | 36 | 9 | 29 |
| 6.00 | 1 | 14 | 30 | 9 | 35 | 12 | 34 |
| 7.00 | 5 | 14 | 26 | 14 | 34 | 17 | 41 |

What is claimed is:

1. A process for the preparation of an aromatic carbonate comprising the steps of:
    A. reacting a silyl ether corresponding to the formula $(CH_3O)_mSiR_{4-m}$ or $R'_3SiOSiR'_3$ wherein R is hydrogen, $C_{1-6}$ alkyl or haloalkyl, R' is $C_{1-6}$ alkyl or haloalkyl and m is an integer from one to three with an aromatic hydroxyl containing compound of the formula $Ar(OH)_n$, wherein Ar is a $C_{6-20}$ aromatic or halo or $C_{1-6}$ alkyl substituted aromatic radical, and n is one or two to prepare an aryl silyl ether or an arylene bis(silyl ether);
    B. reacting dimethyl carbonate with at least a portion of the aryl silyl ether or arylene bis(silyl ether) of step A to prepare a methyl aryl carbonate or an arylene bis(methyl carbonate) and a methyl silyl ether; and
    C. recycling at least a portion of the methyl silyl ether produced in step B for use as the silyl ether reactant in step A.

2. A process according to claim 1, wherein the temperature in step A is from 20° C. to about 100° C.

3. A process according to claim 1, wherein the dimethyl carbonate and aryl silyl ether or arylene bis(silyl ether) are reacted by contacting in the presence of a catalyst.

4. A process according to claim 3, wherein the catalyst is a Lewis acid.

5. A process according to claim 4, wherein the Lewis acid corresponds to the formula $R''_pX(OR'')_{y-p}$, wherein R'' independently each occurrence is hydrocarbyl of from 1 to 10 carbons, X is a tin or titanium ion, p is a number from zero to y equal to the average number of R'' groups, and y is the valence of X.

6. A process for the preparation of aromatic carbonate compounds comprising the steps of:
    A1. reacting methanol with carbon monoxide and oxygen to produce dimethyl carbonate and water;
    A2. reacting a silyl ether corresponding to the formula $(CH_3O)_mSiR_{4-m}$ or $R'_3SiOSiR'_3$ wherein R is hydrogen, $C_{1-6}$ alkyl or haloalkyl, R' is $C_{1-6}$ alkyl or haloalkyl and m is an integer from one to three with an aromatic hydroxyl containing compound of the formula $Ar(OH)_n$, wherein Ar is a $C_{6-20}$ aromatic or halo or $C_{1-6}$ alkyl substituted aromatic radical, and n is one or two to prepare an aryl silyl ether or an arylene bis(silyl ether);
    B. reacting at least a portion of the dimethyl carbonate of step A1 and at least a portion of the aryl silyl ether or arylene bis(silyl ether) of step A2 to prepare a methyl aryl carbonate or an arylene (bis methyl carbonate) and a methyl silyl ether; and
    C. recycling at least a portion of the methyl silyl ether produced in step B for use as the silyl ether reactant in step A2.

7. A process according to claim 6, wherein step B is performed in the presence of a Lewis acid.

8. A process according to claim 7, wherein the Lewis acid corresponds to the formula $R''_pX(OR'')_{y-p}$, wherein R'' independently each occurrence is hydrocarbyl of from 1 to 10 carbons, X is a tin or titanium ion, p is a number from zero to y equal to the average number of R'' groups, and y is the valence of X.

9. A process for the preparation of an aromatic polycarbonate, comprising the steps of:
    A. reacting a silyl ether corresponding to the formula $(CH_3O)_mSiR_{4-m}$ or $R'_3SiOSiR'_3$ wherein R is hydrogen, $C_{1-6}$ alkyl or haloalkyl, R' is $C_{1-6}$ alkyl or haloalkyl and m is an integer from one to three with an aromatic hydroxyl containing compound of the formula $Ar(OH)_n$, wherein Ar is a $C_{6-20}$ aromatic or substituted aromatic radical, and n is one or two to prepare an aryl silyl ether or an arylene bis(silyl ether);
    B. reacting dimethyl carbonate with at least a portion of the aryl silyl ether or arylene bis(silyl ether) of step A to prepare a methyl aryl carbonate or an arylene bis(methyl carbonate) and a methyl silyl ether;

C. recycling at least a portion of the methyl silyl ether produced in step B for use as the silyl ether reactant in step A; and D. converting the methyl aryl carbonate or arylene bis(methyl carbonate) product of step B to an aromatic polycarbonate.

10. A process for the preparation of an aromatic polycarbonate, comprising the steps of:

A1. reacting methanol with carbon monoxide and oxygen to produce dimethyl carbonate and water;

A2. reacting a silyl ether corresponding to the formula $(CH_3O)_m SiR_{4-m}$ or $R'_3SiOSiR'_3$ wherein R is hydrogen, $C_{1-6}$ alkyl or haloalkyl, R' is $C_{1-6}$ alkyl or haloalkyl and m is an integer from one to three with an aromatic hydroxyl containing compound of the formula $Ar(OH)_n$, wherein Ar is a $C_{6-20}$ aromatic or substituted aromatic radical, and n is one or two to prepare an aryl silyl ether or an arylene bis(silyl ether);

B. reacting at least a portion of the dimethyl carbonate of step A1 and at least a portion of the aryl silyl ether or arylene bis(silyl ether) of step A2 to prepare a methyl aryl carbonate or an arylene (bis methyl carbonate) and a methyl silyl ether;

C. recycling at least a portion of the methyl silyl ether produced in step B for use as the silyl ether reactant in step A2; and D. converting the methyl aryl carbonate or arylene bis(methyl carbonate) product of step B to an aromatic polycarbonate.

* * * * *